United States Patent [19]

Hayashi

[11] Patent Number: 4,985,207

[45] Date of Patent: Jan. 15, 1991

[54] BIOCHEMICAL REACTION ANALYZING APPARATUS

[75] Inventor: Hidechika Hayashi, Yokohama, Japan

[73] Assignee: Tosoh Corporation, Shinnanyo, Japan

[21] Appl. No.: 503,109

[22] Filed: Mar. 30, 1990

Related U.S. Application Data

[63] Continuation of Ser. No. 150,655, filed as PCT JP87/00362 on Jun. 9, 1987, published as WO87/07727 on Dec. 17, 1987, abandoned.

[30] Foreign Application Priority Data

Jun. 10, 1986 [JP] Japan ............................... 61-134447

[51] Int. Cl.$^5$ .......................................... G01N 35/04
[52] U.S. Cl. .................................. 422/102; 422/104; 422/58; 422/63; 422/65
[58] Field of Search .................. 422/102, 104, 58, 63, 422/65

[56] References Cited

U.S. PATENT DOCUMENTS 4,595,562 6/1986 Liston et al. ............... 422/102 X
4,595,563 6/1986 Degrave ....................... 422/102 X

FOREIGN PATENT DOCUMENTS 53-106356 8/1978 Japan .
55-11556 3/1980 Japan .
56-52811 12/1981 Japan .

Primary Examiner—Robert J. Warden
Assistant Examiner—Lynn M. Kummert
Attorney, Agent, or Firm—Oblon, Spivak, McClelland, Maier & Neustadt

[57] ABSTRACT

A biochemical reaction measuring apparatus wherein many cups providing reaction cells for biochemical reaction measurement are held and conveyed in arrays on a carrying plate, a cup unloading mechanism is installed which hangs up and unloads the cups from the carrying plate after the measuring processes have been completed, and the cup unloading mechanism has channels into which the cups on the carrying plate being conveyed are fitted automatically and bar members which are engaged with the cups to be hung up at both sides of channels.

8 Claims, 3 Drawing Sheets

BIOCHEMICAL REACTION ANALYZING APPARATUS

This application is a continuation of application Ser. No. 150,655, filed as PCT JP87/00362 on Jun. 9, 1987, published as W087/07727 on Dec. 17, 1987, now abandoned.

TECHNICAL FIELD

The present invention relates to a biochemical reaction measuring apparatus which can perform measurement of many specimens, using biochemical reactions, such as immunological reactions, particularly a biochemical reaction measuring apparatus which can perform such measurements automatically and continuously.

BACKGROUND ART

Recently, much attention has been devoted to biochemical reaction measuring apparatuses which can detect very small amounts of biochemical substances by using immunological and other techniques. For example, immunological measuring apparatuses have been applied to diagnostic kits and others.

In general, such biochemical reaction measurements are performed by making reaction between very small amounts of specimens and reagents etc. in certain reaction cells or recipients, and by using optical techniques to detect and measure the reaction. However, such measurement procedures have a problem that the analysis accuracy greatly depends upon minimizing any errors produced in the pippeted quantities of specimens, reagents etc., though the procedures themselves are monotonous and relatively simple. Consequently, it is difficult for medical technologists to treat many specimens with high accuracy for many hours and there is a possibility of errors in measurements due to the differences in their personal skills. Thus, there has been a great demand for mechanizing these measuring procedures.

Under these circumstances, the inventors have proposed the biochemical reaction measuring apparatuses equipped with a series of systems which can be effectively used for measurements for many specimens.

These biochemical reaction measuring apparatuses have been provided to treat many specimens conveniently, and they are designed such that cups (recipients) of many types prepared to provide many independent reaction cells for different biochemical reactions are fitted and held in holes formed in arrays on carrying plates and the sample pippeting, reaction processing, and reaction analyzing processes are performed in sequence while the carrying plates with cups are transported on the conveying paths.

On the conveying paths in the biochemical reaction analyzing apparatuses as described above, such processes can be also performed in general as seal breaking of cup sealing sheets, pippeting of reaction substances (reagents, antibodies, etc.), separation and cleaning of extra reaction substances, pippeting of substrates reacting with enzymes according to the biochemical reaction marker, agitation, etc. In addition, it is preferred that the conveying paths are equipped with thermostatic means for carrying out a series of processes under predetermined temperature conditions.

In the biochemical reaction measuring apparatus equipped with the mechanized system as described above, it is practical that many of cups are disposed of as waste after the completion of measuring processes and that the carrying plates which have held and carried the cups are reused for the measurement of new specimens.

From this point of view, it is desired that the apparatuses will be more mechanized and automatized by providing them with a mechanism which can remove and throw away the carried cups from the above-described carrying plate at the end of the carrying path. However, the mechanisms of chuck type and sucking head type as normally devised present the disadvantage that they are complicated in construction and low in working efficiency.

An object of the present invention is to operate and utilize more conveniently in practice the biochemical reaction measuring apparatuses equipped with the mechanized system wherein many cups are arrayed and submitted to measuring processes in order according to the protocol.

Another object of the present invention is to provide a biochemical reaction measuring apparatus equipped with a cup unloading mechanism which can remove all cups together from a carrying plate at the end of the above-described system after the cups are used as the reaction cells in which the predetermined biochemical reactions are produced while they are being held and transported in arrays on the plate, and which can be conveniently applied to the mechanization and automatization of the apparatus.

DISCLOSURE OF INVENTION

To achieve these objects, the immunological measuring apparatus according to the present invention is characterized by the facts that at least one array of cups providing biochemical reaction cells are carried on a carrying plate which is transported in the direction of the cup array to perform measurements of biochemical reactions, that it is equipped with a cup unloading mechanism at the position where the transportation of the carrying plate ends, and that the cup unloading mechanism comprises channels into which the top parts of the cups on the carrying plate are fitted at the end position of transportation thereof, and cup hanging means which is composed of bar members placed at both sides of each channel and having side edge parts to engage with and hangs the array of cups fitted in the channel.

In the construction as described above, it is often preferable that the carrying plate is a metal plate such as stainless steel plate, or a metal-plastic combined plate. The carrying plate may be provided with holes in which the cups are fitted and held. The cup holding holes may be formed at least in one array.

The cups are generally plastic recipients, which are prepared and used as reaction cells to measure specimens for individual measurements. To be used for an immunological reaction measurement, the cups may be prepared which already contain a specific antibody (antigen or anti-antibody) held on their inside walls, or insoluble carriers such as beads, so as to assure a high efficiency in measuring processes.

The cup unloading mechanism according to the present invention comprises cup hanging means which is provided with channels (elongated grooves) into which the top parts of the cups held on the carrying plate are fitted so as to be hung in the channels.

The cup hanging means with channels may be, for example, fork-like members, or flat-plate type members provided with longitudinal channels formed on the lower sides of the flat plates. However, both ends of the channel must be opened so that the cups may be both moved into and out of the channels by movement in the same direction. In the cup hanging means, the bar members which define the channels at both sides thereof are provided in such a form that the cups can be engaged with and hung by the side edge parts of the bar members. Therefore, it is convenient that the cups are provided with flanges projecting outside in the top parts of the cups and that the side edges of the bar members at both sides of the channels are provided with a step formed to engage with the lower face of the flange.

To lift the arrays of cups held by the cup hanging means up from the carrying plate, driving means for moving the cup hanging means may be provided; for example, a driving gear which can pivot the cup hanging means around its opposite end to its opened end, or otherwise a lifting mechanism to move the cup hanging means vertical may be used. These driving means may be properly composed of an ordinary link mechanism, a cam mechanism, guide rails, motor and cylinders.

The cups may be unloaded from the cup hanging means simply by tilting the cup hanging means to slide the cups down out of the channels.

To separate the carried cups from the carrying plate, the fixed cup hanging means and a carrying plate lowering mechanism installed at the position where the horizontal transportation of the carrying plate terminates may be used in combination.

The cups may be also unloaded by using the next carrying plate which pushes the cups held by the cup hanging means out of the channels in the opposite direction.

BEST MODE FOR CARRYING OUT THE INVENTION

Figure 4:
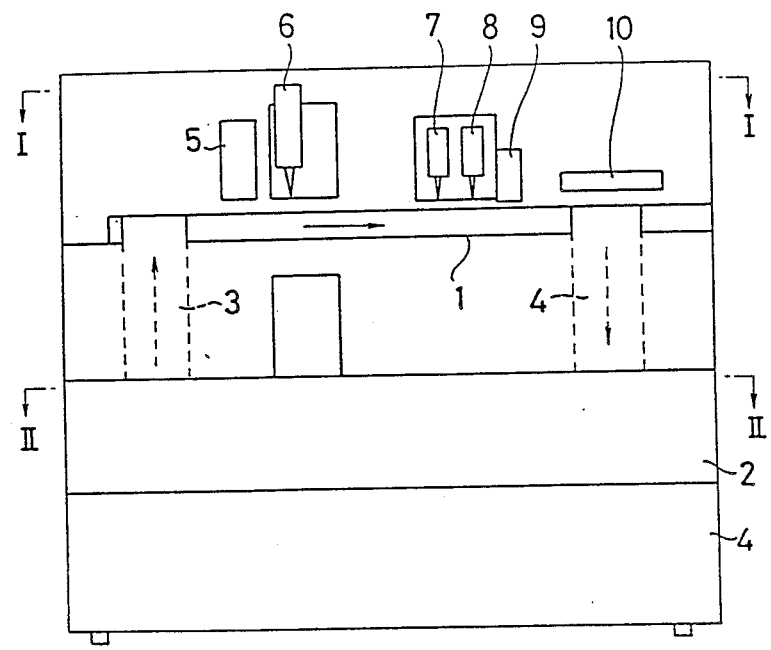
FIG. 4 shows an embodiment of immunological reaction analyzing apparatus according to the present invention to illustrate the configuration of the system.

The present invention will be described in detail by using the embodiment according to the present invention which is applied to the immunological reaction analyzing apparatus as shown in FIG. 4.

FIG. 4 illustrates the configuration of an embodiment according to the present invention. In the figure, 1 is a conveying path, 2 is a storage in which many cups are prepared and stored, and 3 and 4 are lifting and lowering elevators installed at the upstream and downstream ends of the conveying path 1 respectively. A carrying plate with the required cups is lifted by the lifting elevator 3 from the storage 2 up to the conveying path 1, conveyed on the path 1 to the end position thereof at a predetermined timing, and after the cups on the carrying plate have been unloaded by a cup unloading mechanism 10, returned by the lowering elevator 4 to the storage 2 where new cups are loaded on the carrying plate.

In this embodiment, a seal breaker 5, a fractional sample pippeter 6, a B/F separator 7, a substrate pippeter 8 and a fluorescence detector 9 are installed in sequence on the conveying path 1 in the direction of transportation to perform the respective measuring processes for the cups on the carrying plate.

Figure 1:
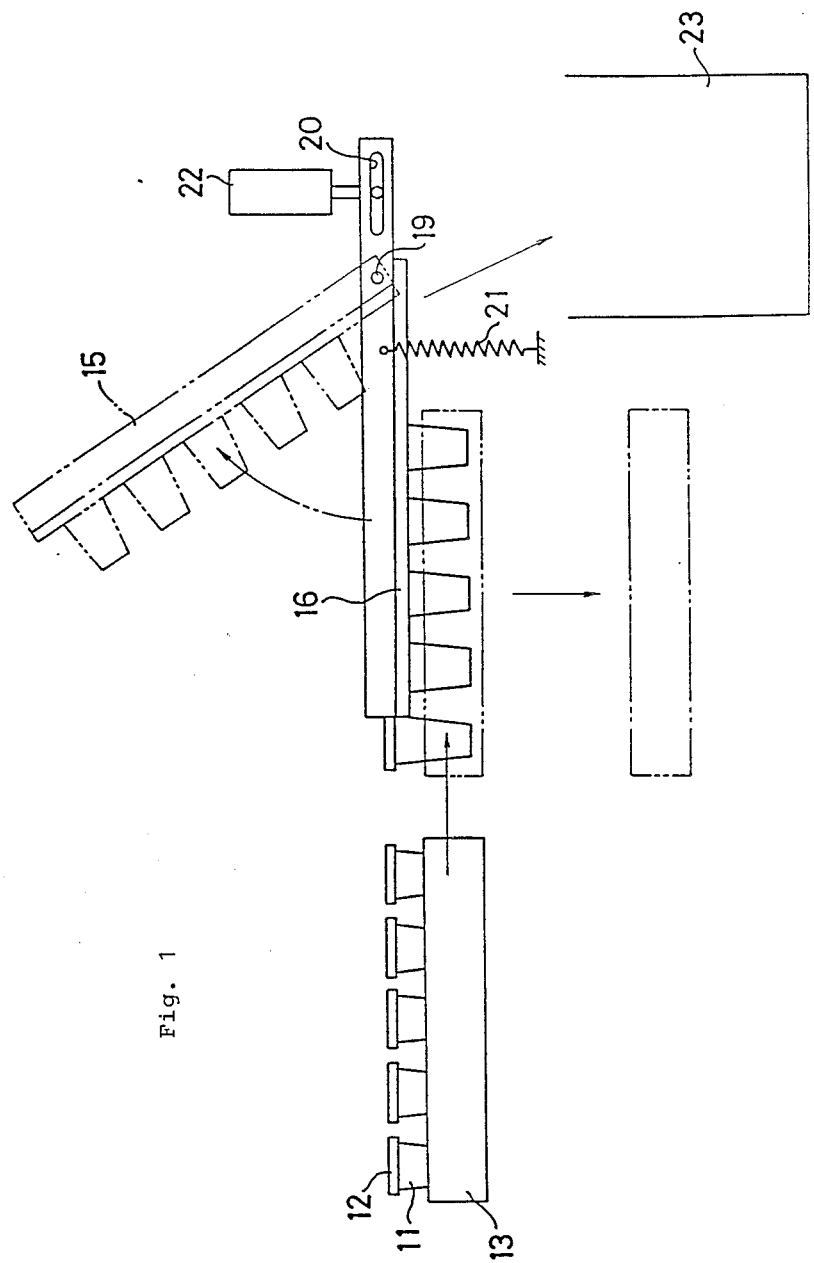
FIG. 1 illustrates the operations of the cup unloading mechanism and the carrying plate.
Figure 2:
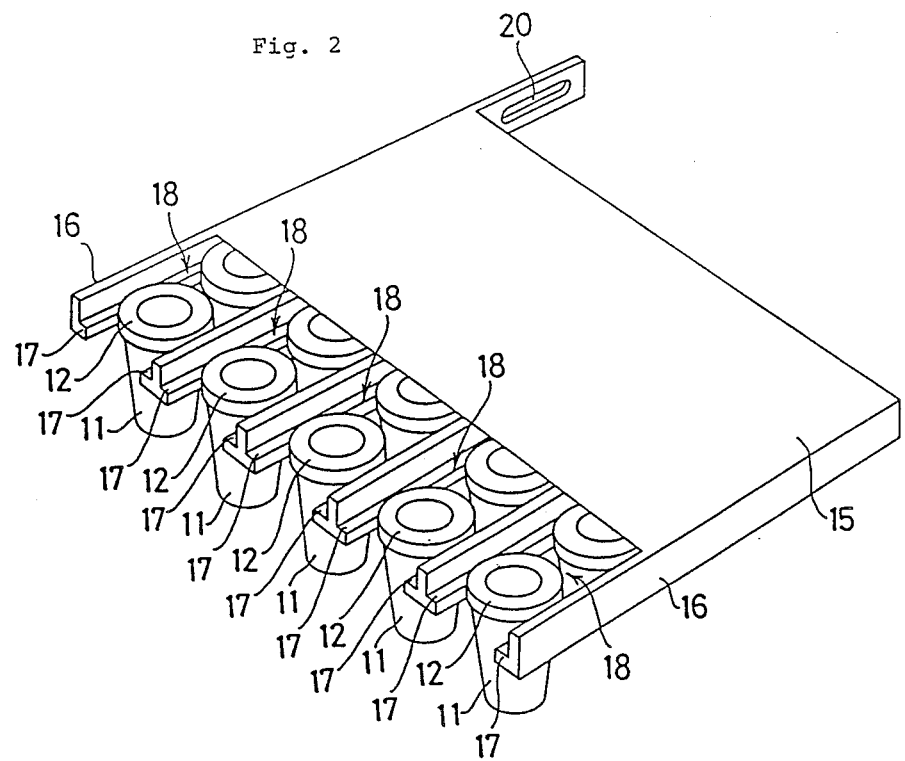
FIG. 2 is a perspective view showing the cup hanging means with arrays of cups fitted in it.
Figure 3:
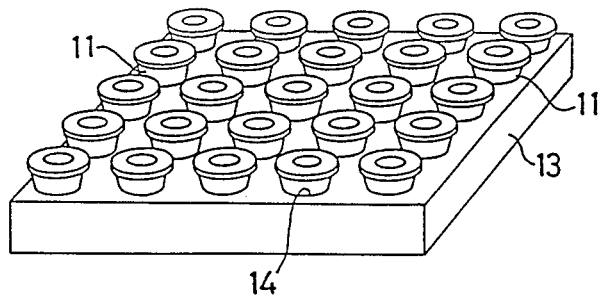
FIG. 3 is a perspective view showing the carrying plate with arrays of cups held on it.

FIGS. 1 and 2 show an embodiment of cup unloading mechanism according to the present invention to illustrate its construction and operation. In this embodiment, a cup hanging plate 15 is provided with channels (or elongated grooves) 18 defined by the bar type parts 16 and the lower face of the flat-plate type part of the plate 15. The bar type parts 16 which define the channels 18 are extended a predetermined length beyond the end of the flat-plate type part of the plate 15. In the lower part of each bar type part 16, two lower edge flanges 17 are formed to project into the two channels 18 at both sides of the bar type part 16 respectively. As it is shown in FIG. 2, the peripheral flange 12 in the top part of each cup 11 held on the carrying plate 13 is engaged with the two lower edge flanges 17 of the adjacent bar type parts 16 so as to be conveniently hung and lifted.

In this embodiment, the cup hanging plate 15 is rotatably supported by a shaft 19 mounted on a fixed part (not shown) near the opposite side of the plate 15 to the side thereof from which the carrying plate 13 is conveyed under the cup hanging plate 15. The cup hanging plate 15 is normally stationed by a return spring 21 at its initial position as shown by the solid lines in FIG. 1. At the initial position, the cup hanging plate 15 is in a position to receive the arrays of cups 11 on the running carrying plate 13 into the channels 18.

A long groove 20 is formed in the extended part of the cup hanging plate 15 on the side thereof as described above, and engaged with the end of the plunger in an air cylinder assembly 22 so that the cup hanging plate 15 can be pivoted to the position as shown by the dotted lines in FIG. 1. At the tilted position, the cup hanging plate 15 hangs the arrays of cups 11 fitted in the holes 14 formed on the carrying plate 13, and slides the cups 11 out of the channels 18 down into a waste cup receiver 23.

In this embodiment thus constructed, many cups held in arrays on the carrying plate being conveyed can be automatically fitted into the channels 18 in the cup hanging plate 15, lifted up together by the cup hanging plate 15 tilted or pivoted by the air cylinder assembly 22 which is driven by a control circuit (not shown) at the predetermined timing, and slided down into the waste receiver 23. Therefore, the present invention presents the advantages that the carrying plate can be readily reused and that almost no maintenance and inspection are required because of the simple construction.

INDUSTRIAL APPLICABILITY

As it has been described above, the biochemical reaction measuring apparatus according to the present invention present the advantages that the cup unloading mechanism installed at the position where the transportation of the carrying plate terminates can unload automatically all the cups on the carrying plate after the cups are used as the reaction cells in which the predetermined biochemical reactions are produced while they are being held and transported on the carrying plate, and that the cup unloading mechanism is applicable to be built in an automatized biochemical reaction measuring apparatus.

What is claimed is:

1. A biochemical reaction measuring apparatus which performs biochemical reaction measuring processes, including a carrying plate carrying thereon at least one array of cups providing biochemical reaction cells, means for conveying said carrying plate substantially horizontally in the direction of the cup array, and a cup unloading mechanism at a position where the substantially horizontal transportation of said carrying plate terminates, said cup unloading mechanism comprising:

means for forming open ended channels, each of said channels having two open ends and into which top parts of said cups on said carrying plate are fitted at said position where transportation terminates, and cup hanging means comprising bar members placed at both sides of said channels and having side edge parts to engage with and hang said arrays of cups fitted in said channels, whereby cups can be both moved into and out of said channels by movement in the same direction.

2. A biochemical reaction measuring apparatus according to claim 1, including driving means for moving said cup having means between a position where said arrays of cups are fitted into said channels and a position where said arrays of cups are lifted up and discharged out of said channels.

3. A biochemical reaction measuring apparatus according to claim 2, wherein said driving means comprises means for pivoting said cup hanging means around an axis transverse to the longitudinal direction of said channels.

4. A biochemical reaction measuring apparatus according to claim 1, including lowering mechanism for lowering said carrying plate installed at the position where the horizontal transportation of said carrying plate terminates and wherein said cup hanging means is fixed.

5. A biochemical reaction measuring apparatus according to claim 1 or 4, wherein said carrying plate holds a plurality of arrays of cups.

6. A biochemical reaction measuring apparatus according to claim 1, wherein said cups have peripheral flanges in their top parts which can be engaged with said side edge parts of said bar members which constitute said cup hanging means.

7. A biochemical reaction measuring apparatus according to claim 1, wherein said cup hanging means comprises a flat-plate type member provided with said channels formed in a lower face thereof.

8. A biochemical reaction measuring apparatus, comprising:
    (a) reaction cups having upper openings sealed for providing a space for a reaction,
    (b) a transfer block for carrying the reaction cups,
    (c) transporting means for transporting the transfer block,
    (d) means for breaking the seal sealing the upper openings of the reaction cups,
    (e) means for pouring a sample to be measured into the reaction cups,
    (f) means for pouring reagent to react with the sample into the reaction cups,
    (g) means for measuring a signal produced by the reaction between the sample and the reagent,
    (h) means for discharging the reaction cups from the transfer block after the measurement, wherein the discharging means has driving means for tilting the transfer block,
    (i) means for receiving the cups discharged from the transfer block, and
    (j) lifting-up or lifting-down means arranged on both ends of the transporting means,
    whereby the reaction cups carried by the transfer block are transported by the transporting means and are subjected to the operations of the seal breaking means, the sample pouring means, the reagent pouring means, the measuring means and finally discharged by the discharging means from the transfer block, and the empty block is lifted down and recycled for further measurement.

* * * * *